(12) United States Patent
Farin

(10) Patent No.: US 7,601,150 B2
(45) Date of Patent: Oct. 13, 2009

(54) METHOD AND APPARATUS FOR PLASMA SURGERY

(75) Inventor: Günter Farin, Tübingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 1031 days.

(21) Appl. No.: 10/481,692

(22) PCT Filed: Jun. 20, 2002

(86) PCT No.: PCT/EP02/06858

§ 371 (c)(1),
(2), (4) Date: Dec. 19, 2003

(87) PCT Pub. No.: WO03/000150

PCT Pub. Date: Jan. 3, 2003

(65) Prior Publication Data

US 2004/0181220 A1  Sep. 16, 2004

(30) Foreign Application Priority Data

Jun. 22, 2001  (DE) ................ 101 29 685

(51) Int. Cl.
*A61B 18/12*  (2006.01)
(52) U.S. Cl. .......................... 606/40; 606/49
(58) Field of Classification Search ........... 606/49, 606/40
See application file for complete search history.

(56) References Cited

U.S. PATENT DOCUMENTS

| | | | |
|---|---|---|---|
| 2,828,748 A | 4/1958 | August ............. | 128/303.14 |
| 4,781,175 A * | 11/1988 | McGreevy et al. ............ | 606/40 |
| 5,330,469 A | 7/1994 | Fleenor ....................... | 606/40 |
| 6,197,026 B1 | 3/2001 | Farin et al. .................... | 606/49 |
| 6,206,878 B1 | 3/2001 | Bishop et al. ................. | 606/49 |
| 7,131,969 B1 * | 11/2006 | Hovda et al. .................. | 606/45 |

FOREIGN PATENT DOCUMENTS

| | | |
|---|---|---|
| DE | 11 59 574 B | 12/1963 |
| DE | 41 39 029 C2 | 6/1993 |
| DE | 197 06 270 A1 | 9/1997 |
| GB | 1 014 995 | 12/1965 |
| GB | 1014995 | 12/1965 |
| GB | 2 311 226 | 9/1997 |
| JP | 10-151142 | 6/1998 |
| WO | WO-98/35618 | 8/1998 |

OTHER PUBLICATIONS

Farin, Grund, "Technology of Argon Plasma Coagulation with Particular Regard to Endoscopic Applications", *Endoscopic Surgery and Allied Technologies*, vol. 2, Feb. 1994.
Grund, Storek, and Farin, "Endoscopic Argon Plasma Coagulation (APC) First Clinical Experiences in Flexible Endoscopy", *Endoscopic Surgery and Allied Technologies*, vol. 2, Feb. 1994.
International Search Report in PCT/EP02/06858 dated Oct. 7, 2002.

* cited by examiner

*Primary Examiner*—Lee S Cohen
(74) *Attorney, Agent, or Firm*—Dickstein Shapiro LLP

(57) ABSTRACT

An apparatus for argon-plasma coagulation (APC) is disclosed, in which after activation of the apparatus for APC a specified amount of noble gas flows out of the APC instrument before the high-frequency voltage for ionizing the noble gas is switched on, or can be switched on. As a result an increase in safety is achieved.

22 Claims, 1 Drawing Sheet

Delay time = preliminary argon flow

METHOD AND APPARATUS FOR PLASMA SURGERY

RELATED U.S. APPLICATIONS

This is the U.S. national phase of International Application No. PCT/EP02/006858 filed Jun. 20, 2002 and designating the United States, the entire disclosure of which is incorporated herein by reference.

FIELD OF THE INVENTION

The disclosed embodiments relate to a method and apparatus for plasma surgery.

BACKGROUND OF THE INVENTION

Plasma surgery is a form of high-frequency surgery in which a high-frequency electrical alternating current (HF current) is passed through electrically ionized and consequently electrically conductive noble gas (plasma), in particular argon (argon plasma) or helium (helium plasma), and applied to the tissue to be treated in order to produce surgically relevant thermal effects in this target tissue. The noble gas that has most often been used for this purpose is argon, and the best-known thermal effect in the tissue is coagulation, for which reasons this procedure is also known as "argon-plasma coagulation (APC)". In principle other gases or gas mixtures could be used instead of a noble gas for plasma surgery. For example, for over 50 years air has been used as the gas, in which case the procedure is known as fulguration or spray-coagulation. However, noble gases offer the advantage that they do not cause any chemical effects, i.e. they have a chemically neutral behavior. This advantage can be utilized in particular for the endoscopic application of plasma surgery, where the view would be obstructed by unavoidable smoke formation if air were employed, and the burning or vaporization of biological tissue inevitably associated with the use of air could lead to severe complications, such as the perforation of organ walls.

For both open incisions and minimally invasive operations plasma surgery has been used for more than 20 years primarily to stop bleeding by thermal means, namely by means of the thermal coagulation of the biological tissue. In this process either the air already present serves as the required gas, as in the case of fulguration or spray coagulation, or a noble gas is used, in which case the procedure is called argon-plasma coagulation because the gas most often used is argon.

Since catheter-like, flexible instruments have been developed for APC, which can be inserted through a working or instrumentation channel of flexible endoscopes (G. Farin et al.: Technology of Argon Plasma Coagulation with Particular Regard to Endoscopic Applications; Endoscopic Surgery and Allied Technologies, No. 1, Vol. 2, February 1994, 71-77), APC can also be used in flexible endoscopy. It soon became clear that there is a broad spectrum of indications for the APC procedure in this area. Apart from thermal hemostasis, APC is used in flexible endoscopy for tasks such as the thermal destruction or thermal devitalization of pathological tissue (Grund K. E., Storek D., Farin G.: Endoscopic Argon Plasma Coagulation (APC)—First Clinical Experiences in Flexible Endoscopy. Endoscopic Surgery and Allied Technologies, No. 1, Vol. 2, February 1994, 42-46). Although the term argon-plasma coagulation (APC) is now too narrow in view of the recent indications for this procedure in flexible endoscopy, and "plasma surgery" would be more suitable, here "argon-plasma: coagulation (APC)" will continue to be used for this procedure, but without limiting the procedure to the noble gas argon or to coagulation as the thermal effect.

The apparatus available since 1992 for application of APC in flexible endoscopy is described in the German patent DE 41 39 029.

A known problem in employing thermal methods within the gastrointestinal tract, as well as in the tracheobronchial system and the throat region, is the risk that combustible or even explosive substances will be unintentionally ignited. The gastrointestinal tract may contain combustible endogenous gases that can be ignited by the relatively high temperature of the plasma. In the tracheobronchial system the respired gas may have a high oxygen concentration or the patient may even be breathing pure oxygen, so that ignition of combustible substances by the hot plasma can result in an intense fire. Several cases of damage caused in this way are known, both with and without a lethal outcome. Although noble gases cannot cause a fire, damage by fire and/or explosions has been known to occur even when APC is being used.

BRIEF SUMMARY OF THE INVENTION

The object of the disclosed embodiments is to improve devices for APC in such a way that the ignition of combustible substances is avoided.

This object is achieved in that after the device for APC has been activated, for example by a pedal or a finger-operated switch, a specified amount of argon flows out of the distal end of the particular APC instrument or APC probe Pr being used, which reduces the concentration of the combustible gas, e.g. carbon monoxide (CO), and/or the concentration of a gas such as oxygen ($O_2$) that causes the burning of the combustible gas, to such an extent that ignition of this gas mixture is impossible. In the following, this amount of argon is termed the preliminary argon flow.

According to a disclosed embodiment, there is provided a method of operating an apparatus for argon-plasma coagulation (APC), the apparatus comprises at least a high-frequency source, a source of noble gas, and an APC instrument connected to the high-frequency source and to the source of the noble gas, wherein the method comprises activating the apparatus for APC; after activation of the apparatus for APC, causing a specified amount of noble gas to flow out of the APC instrument, thereby reducing the concentration of combustible substances near a biological tissue to be treated and thus avoiding ignition of the combustible substances; and after causing the specified amount of the noble gas to flow out of the APC instrument, allowing a high-frequency voltage for ionizing the noble gas is switched on, wherein the high-frequency voltage cannot be turned on as long as the specified amount of the noble gas has not flowed out of the APC instrument.

According to another disclosed embodiment, there is provided an apparatus for argon-plasma coagulation (APC), comprising a high-frequency source; a source of a noble gas; an argon-plasma coagulation instrument connected to the high-frequency source and to the source of the noble gas to conduct a coagulation current from the high-frequency source into the gas and through the gas into biological tissue to coagulate the tissue; a controllable gas valve attached to the noble gas source; at least one gas-flow sensor for determining a flow rate of the noble gas from the source; and control means for controlling the flow rate of the noble gas from the noble gas source to the instrument such that after activation of the apparatus a specified amount of noble gas must flow out of the instrument before the high-frequency source for ionizing the noble gas can be switched on, thereby reducing the concentration of combustible substances near a biological tissue to be treated and thus avoiding ignition of the combustible substances, and wherein the control means is adapted to prevent the high-frequency source from being turned on until the specified amount of the noble gas has flowed out of the argon-plasma coagulation instrument.

According to yet another embodiment, there is provided a method of operating an apparatus for argon-plasma coagulation (APC), wherein the apparatus comprises at least a high-frequency source, a source of noble gas, and an APC instrument connected to the high-frequency source and to the source of the noble gas, and wherein the method comprises activating the apparatus for APC; after activation of the apparatus for APC, causing a specified amount of noble gas to flow out of the APC instrument, thereby reducing the concentration of combustible substances near a biological tissue to be treated and thus avoiding the ignition of the combustible substances; and after causing the specified amount of the noble gas to flow out of the APC instrument, allowing a high-frequency voltage for ionizing the noble gas to be switched on, wherein a flow rate at which the noble gas flows out of the APC instrument after activation of the apparatus but before the high-frequency voltage is turned on is higher than a flow rate at which the noble gas flows out of the APC instrument after the high-frequency voltage has been turned on during an APC procedure.

According to yet another embodiment, there is provided an apparatus for argon-plasma coagulation (APC), comprising a high-frequency source; a source of noble gas; an argon-plasma coagulation instrument connected to the high-frequency source and to the source of the noble gas to conduct a coagulation current from the high-frequency source into the gas and through the gas into biological tissue to coagulate the tissue; a controllable gas valve attached to the noble gas source; at least one gas-flow sensor for determining a flow rate of the noble gas from the source; and control means for controlling the flow rate of the noble gas from the noble gas source to the instrument such that, after activation of the apparatus, a specified amount of the noble gas is permitted to flow out of the instrument before the high-frequency source for ionizing the noble gas is switched on, thereby reducing the concentration of combustible substances near a biological tissue to be treated and thus avoiding the ignition of the combustible substances, wherein the control means controls the flow rate of the noble gas from the noble gas source to the instrument such that the flow rate is higher after activation of the apparatus but before the high-frequency source is switched on than it is after the high-frequency source has been turned on during an argon-plasma coagulation procedure.

To minimize the time delay $\Delta t$ until APC initiation that is caused by the preliminary argon flow, it is useful to make this preliminary flow rate as high as possible; as a rule it can be higher (high) than the flow rate of the argon employed for the APC (low). It can be advantageous here for the amount of preliminary argon to be dependent on relevant boundary conditions; this variation can be achieved either by manual parameter setting before APC is carried out or by a control system with automatic monitoring of the boundary conditions. For example, the amount of preliminary argon can be specified as proportional to the oxygen concentration in the respired gas, or can be automatically controlled or regulated. Similarly, the amount of preliminary oxygen can also be made proportional to the duration of the pause between two or more activations of the procedure and/or to the duration of the activations of APC themselves, by prior adjustment or by a control or regulation means.

DETAILED DESCRIPTION OF THE INVENTION

Reference is hereby made to the attached drawings wherein an apparatus suitable for achieving the stated objective comprises an argon source Ar, for instance a gas cylinder, which is equipped with at least one controllable gas valve V and at least one gas-flow sensor Se that can be used for manual setting of both the preliminary argon flow and the flow rate needed to a coagulation instrument or probe Pr for APC. The instrument or probe Pr is adapted to conduct a coagulation current from a high-frequency source into the gas and through the latter into biological tissue to coagulate the tissue. For the automatic control and/or regulation of the preliminary argon flow and/or the argon flow rate needed for APC, the hardware is preferably equipped with an on/off switch F and in addition with control and/or regulation means Ct. In another disclosed embodiment the hardware also includes electronic memories and processors, which permit programming and a corresponding automatic control and/or regulation of the preliminary argon flow and/or the argon flow rate needed for APC.

Figure 1:
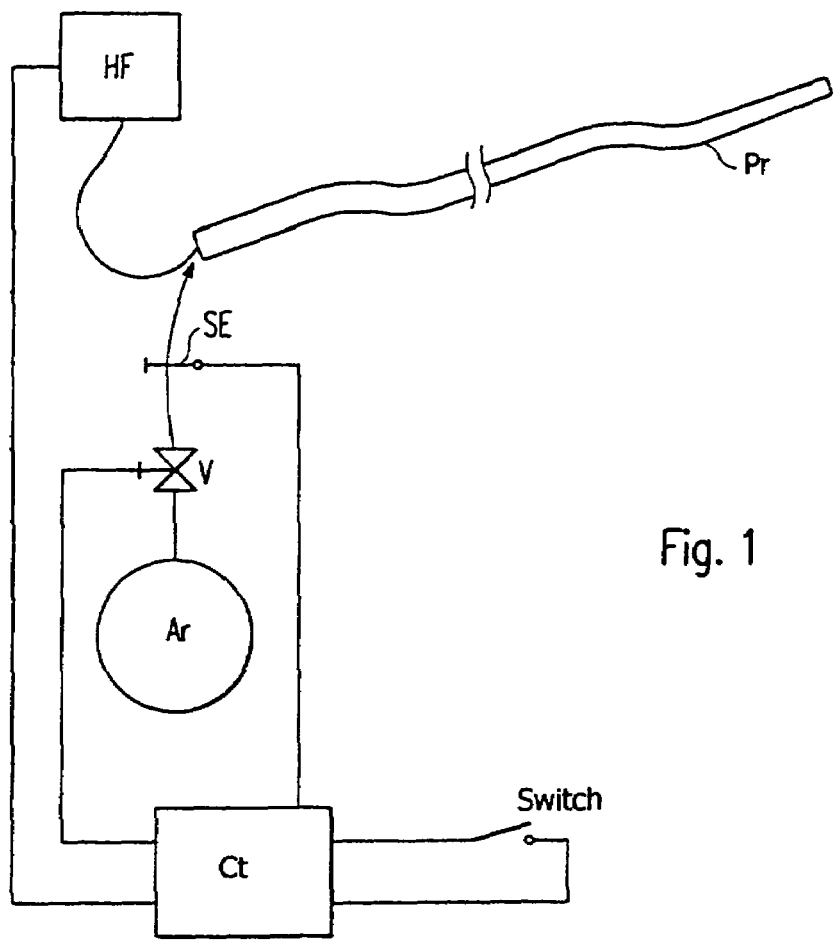
FIG. 1 shows schematically an apparatus for carrying out the method in accordance with disclosed embodiments.
Figure 2:
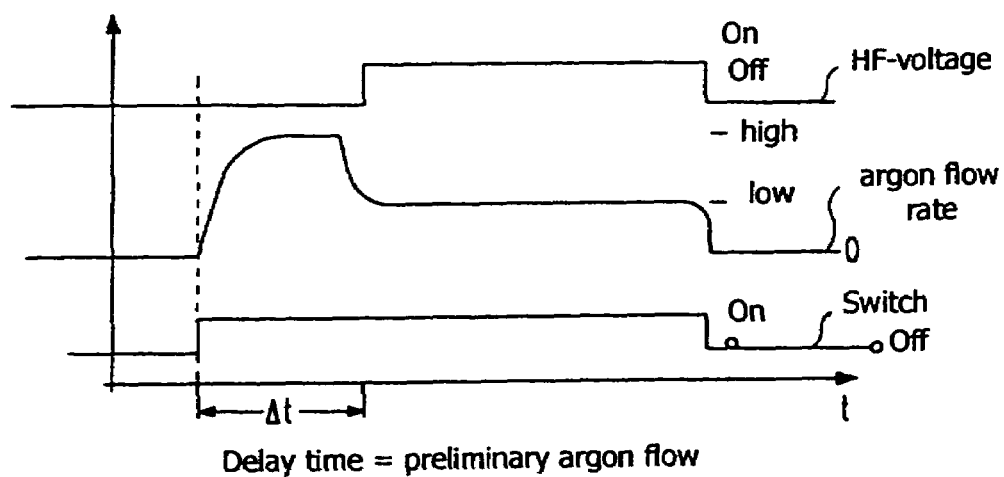
FIG. 2 is a graph showing how the high-frequency voltage and the argon flow rate vary with time when the apparatus shown in FIG. 1 is switched on and off.

In the disclosed embodiments and as shown in FIG. 2, for a predetermined time $\Delta t$ after activation of the switch F for the apparatus, a specified amount of argon Ar is permitted to flow out of the APC instrument Pr before the high-frequency voltage HF for ionizing the gas is switched on. The quantity of argon that flows out of the APC instrument Pr before the high-frequency voltage HF is switched on or can be switched on, can be adjusted in advance by means of the valve V. This quantity is dependent on variable boundary conditions and, preferably, is greater, the longer the pause between two periods of activation or if the preceding periods of activation have been comparatively short. The apparatus is also preferably provided with means for the generation of an acoustic and/or visual signal during the time interval from activation of the apparatus for argon-plasma coagulation until the high-frequency voltage HF is turned on in order to inform the user that the high-frequency voltage has not yet been turned on or that it cannot yet be turned on. The apparatus may also be adapted so that the high-frequency voltage HF is not or cannot be turned on as long as a specified amount of argon has not flowed out of the APC instrument Pr. In addition, the apparatus may comprise control means so that the rate (volume per unit time) at which the argon flows out of the instrument Pr is arranged to be higher after activation of the apparatus but before the high-frequency voltage HF is turned on than it is after the high-frequency voltage HF has been turned on during an APC procedure.

The invention claimed is:

1. A method of operating an apparatus for argon-plasma coagulation (APC), wherein the apparatus comprises at least a high-frequency source, a source of noble gas, and an APC instrument connected to the high-frequency source and to the source of the noble gas, and wherein the method comprises the following steps:

activating the apparatus for APC;

after activation of the apparatus for APC, causing a specified amount of noble gas to flow out of the APC instrument, thereby reducing the concentration of combustible substances near a biological tissue to be treated and thus avoiding the ignition of the combustible substances; and after causing the specified amount of the noble gas to flow out of the APC instrument, allowing a high-frequency voltage for ionizing the noble gas to be switched on, wherein the high-frequency voltage cannot be turned on as long as the specified amount of the noble gas has not flowed out of the APC instrument.

2. A method as claimed in claim 1, wherein the specified amount of the noble gas that flows out of the APC instrument before allowing the high-frequency voltage to be switched on can be adjusted in advance.

3. A method as claimed in claim 1, wherein the specified amount of the noble gas that flows out of the APC instrument before allowing the high-frequency voltage to be switched on is dependent on variable boundary conditions.

4. A method as claimed in claim 3, wherein the specified amount of the noble gas that flows out of the APC instrument before allowing the high-frequency voltage to be switched on is greater, the longer a pause between two periods of activation and/or the shorter preceding periods of activation have been.

5. A method as claimed in claim 1, further comprising, during a time interval from activation of the apparatus for argon-plasma coagulation (APC) until the high-frequency voltage is turned on, generating at least one of an acoustic and a visual signal, which informs the user that the high-frequency voltage is not yet turned on, or that it cannot yet be turned on.

6. An apparatus for argon-plasma coagulation (APC), comprising:
   a high-frequency source;
   a source of noble gas;
   an argon-plasma coagulation instrument connected to the high-frequency source and to the source of the noble gas to conduct a coagulation current from the high-frequency source into the gas and through the gas into biological tissue to coagulate the tissue;
   a controllable gas valve attached to the noble gas source;
   at least one gas-flow sensor for determining a flow rate of the noble gas from the source; and
   control means for controlling the flow rate of the noble gas from the noble gas source to the instrument such that, after activation of the apparatus, a specified amount of the noble gas must flow out of the instrument before the high-frequency source for ionizing the noble gas can be switched on, thereby reducing the concentration of combustible substances near a biological tissue to be treated and thus avoiding the ignition of the combustible substances,
   wherein the control means is adapted to prevent the high-frequency source from being turned on until the specified amount of the noble gas has flowed out of the argon-plasma coagulation instrument.

7. An apparatus according to claim 6, wherein the control means can be adjusted in advance to control the amount of the noble gas that flows out of the argon-plasma coagulation instrument before the high-frequency source can be switched on.

8. A apparatus according to claim 6, wherein the control means is adapted to control the flow rate of the noble gas from the noble gas source to the instrument before the high-frequency source can be switched on, wherein the flow rate is dependent on relevant boundary conditions.

9. An apparatus according to claim 6, wherein the control means is adapted to adjust the amount of the noble gas that can flow out of the argon-plasma coagulation instrument before the high-frequency source can be switched on, where the amount of the noble gas is dependent on a length of a pause between two periods of activation of the instrument and a length of preceding periods of activation of the instrument.

10. An apparatus according to claim 6, comprising signaling means for generating a signal which informs the user that the high-frequency source is not turned on during a time interval between activation of the apparatus for coagulation and a turning on of the high-frequency source.

11. A method of operating an apparatus for argon-plasma coagulation (APC), wherein the apparatus comprises at least a high-frequency source, a source of noble gas, and an APC instrument connected to the high-frequency source and to the source of the noble gas, and wherein the method comprises the following steps:
   activating the apparatus for APC;
   after activation of the apparatus for APC, causing a specified amount of noble gas to flow out of the APC instrument, thereby reducing the concentration of combustible substances near a biological tissue to be treated and thus avoiding the ignition of the combustible substances; and
   after causing the specified amount of the noble gas to flow out of the APC instrument, allowing a high-frequency voltage for ionizing the noble gas to be switched on,
   wherein a flow rate at which the noble gas flows out of the APC instrument after activation of the apparatus but before the high-frequency voltage is turned on is higher than a flow rate at which the noble gas flows out of the APC instrument after the high-frequency voltage has been turned on during an APC procedure.

12. A method as claimed in claim 11, wherein the specified amount of the noble gas that flows out of the APC instrument before allowing the high-frequency voltage to be switched on can be adjusted in advance.

13. A method as claimed in claim 11, wherein the specified amount of the noble gas that flows out of the APC instrument before allowing the high-frequency voltage to be switched on is dependent on variable boundary conditions.

14. A method as claimed in claim 13, wherein the specified amount of the noble gas that flows out of the APC instrument before allowing the high-frequency voltage to be switched on is greater, the longer a pause between two periods of activation and/or the shorter preceding periods of activation have been.

15. A method as claimed in claim 11, further comprising, during a time interval from activation of the apparatus for argon-plasma coagulation (APC) until the high-frequency voltage is turned on, generating at least one of an acoustic and a visual signal, which informs the user that the high-frequency voltage is not yet turned on, or that it cannot yet be turned on.

16. A method as claimed in claim 11, wherein the high-frequency voltage cannot be turned on as long as the specified amount of the noble gas has not flowed out of the APC instrument.

17. An apparatus for argon-plasma coagulation (APC), comprising:
   a high-frequency source;
   a source of noble gas;
   an argon-plasma coagulation instrument connected to the high-frequency source and to the source of the noble gas to conduct a coagulation current from the high-frequency source into the gas and through the gas into biological tissue to coagulate the tissue;

a controllable gas valve attached to the noble gas source;

at least one gas-flow sensor for determining a flow rate of the noble gas from the source; and control means for controlling the flow rate of the noble gas from the noble gas source to the instrument such that, after activation of the apparatus, a specified amount of the noble gas is permitted to flow out of the instrument before the high-frequency source for ionizing the noble gas is switched on, thereby reducing the concentration of combustible substances near a biological tissue to be treated and thus avoiding the ignition of the combustible substances, wherein the control means controls the flow rate of the noble gas from the noble gas source to the instrument such that the flow rate is higher after activation of the apparatus but before the high-frequency source is switched on than it is after the high-frequency source has been turned on during an argon-plasma coagulation procedure.

18. A apparatus according to claim 17, wherein the control means can be adjusted in advance to control the amount of the noble gas that flows out of the argon-plasma coagulation instrument before the high-frequency source is switched on.

19. An apparatus according to claim 17, wherein the control means is adapted to control the flow rate of the noble gas from the noble gas source to the instrument before the high-frequency source is switched on, wherein the flow rate is dependent on relevant boundary conditions.

20. An apparatus according to claim 17, wherein the control means is adapted to adjust the amount of the noble gas that can flow out of the argon-plasma coagulation instrument before the high-frequency source is switched on, where the amount of the noble gas is dependent on a length of a pause between two periods of activation of the instrument and a length of preceding periods of activation of the instrument.

21. An apparatus according to claim 17, comprising signaling means for generating a signal which informs the user that the high-frequency source is not turned on during a time interval between activation of the apparatus for coagulation and a turning on of the high-frequency source.

22. An apparatus according to claim 17, wherein the control means is adapted to prevent the high-frequency source from being turned on until the specified amount of the noble gas has flowed out of the argon-plasma coagulation instrument.

* * * * *

UNITED STATES PATENT AND TRADEMARK OFFICE
CERTIFICATE OF CORRECTION

PATENT NO. : 7,601,150 B2
APPLICATION NO. : 10/481692
DATED : October 13, 2009
INVENTOR(S) : Günter Farin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1668 days.

Signed and Sealed this

Fifth Day of October, 2010

David J. Kappos
*Director of the United States Patent and Trademark Office*